United States Patent
Reinhard et al.

(10) Patent No.: US 9,353,095 B2
(45) Date of Patent: May 31, 2016

(54) CRYSTALLINE FORM A OF 1,5-DIMETHYL-6-THIOXO-3-(2,2,7-TRIFLUORO-3-OXO-4-(PROP-2-YNYL)-3,4-DIHYDRO-2H-BENZO[B][1,4]OXAZIN-6-YL)-1,3,5-TRIAZINANE-2,4-DIONE

(71) Applicant: BASF SE, Ludwigshafen (DE)

(72) Inventors: Robert Reinhard, Limburgerhof (DE); Tiziana Chiodo, Mannheim (DE); Bernd Wolf, Niederkirchen (DE); Stefan Scherer, Osthofen (DE); Matthias Bratz, Maxdorf (DE); Matthias Witschel, Bad Duerkheim (DE); Trevor William Newton, Neustadt (DE); Thomas Seitz, Viernheim (DE)

(73) Assignee: BASF SE, Ludwigshafen (DE)

( * ) Notice: Subject to any disclaimer, the term of this patent is extended or adjusted under 35 U.S.C. 154(b) by 8 days.

(21) Appl. No.: 14/402,518

(22) PCT Filed: May 15, 2013

(86) PCT No.: PCT/EP2013/060028
§ 371 (c)(1),
(2) Date: Nov. 20, 2014

(87) PCT Pub. No.: WO2013/174693
PCT Pub. Date: Nov. 28, 2013

(65) Prior Publication Data
US 2015/0099631 A1    Apr. 9, 2015

Related U.S. Application Data

(60) Provisional application No. 61/651,602, filed on May 25, 2012.

(30) Foreign Application Priority Data

May 25, 2012  (EP) .................................. 12169638

(51) Int. Cl.
*A01N 43/84* (2006.01)
*C07D 413/04* (2006.01)

(52) U.S. Cl.
CPC .............. *C07D 413/04* (2013.01); *A01N 43/84* (2013.01); *C07B 2200/13* (2013.01)

(58) Field of Classification Search
None
See application file for complete search history.

(56) References Cited

FOREIGN PATENT DOCUMENTS

DE   WO 2011057935 A1 *  5/2011  ............. A01N 43/84
WO   WO 2010/145992      12/2010

OTHER PUBLICATIONS

International Preliminary Report on Patentability Nov. 25, 2014 prepared in International Application No. PCT/EP2013/060028.
International Search Report dated Jun. 11, 2013, prepared in International Application No. PCT/EP2013/060028.
European Search Report dated Sep. 2, 2012, prepared in EP Application No. 12169638.

\* cited by examiner

*Primary Examiner* — Mina Haghighatian
*Assistant Examiner* — Erin Hirt
(74) *Attorney, Agent, or Firm* — Brinks Gilson & Lione

(57) ABSTRACT

The present invention relates to a novel crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione. The invention also relates to a process for the production of this crystalline form and formulations for plant protection which contains the novel crystalline form of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

14 Claims, No Drawings

CRYSTALLINE FORM A OF 1,5-DIMETHYL-6-THIOXO-3-(2,2,7-TRIFLUORO-3-OXO-4-(PROP-2-YNYL)-3,4-DIHYDRO-2H-BENZO[B][1,4]OXAZIN-6-YL)-1,3,5-TRIAZINANE-2,4-DIONE

This application is a National Stage application of International Application No. PCT/EP2013/060028, filed May 15, 2013, which claims the benefit of U.S. Provisional Application No. 61/651,602, filed May 25, 2012, the entire contents of which are hereby incorporated herein by reference. This application also claims priority under 35 U.S.C. §119 to European Patent Application No. 12169638.9, filed May 25, 2012, the entire contents of which is hereby incorporated herein by reference.

DESCRIPTION

The present invention relates to a novel crystalline form of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione. The invention also relates to a process for the production of this crystalline form and formulations for plant protection which contains the novel crystalline form of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione.

1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione is the herbicidal active substance of the formula I:

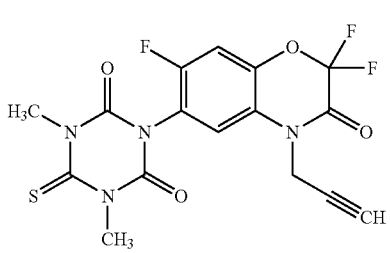

1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, which hereinafter is also termed as benzoxazinone I, and a process for its production are known from WO 2010/145992. This process yields benzoxazinone I as an amorphous solid. A liquid formulation of benzoxazinone I has also been described.

For the production of active substances on the industrial scale but also for the formulation of active substances, in many cases knowledge concerning the possible existence of crystalline modifications (also described as crystalline forms) or of solvates of the active substance in question, and knowledge of the specific properties of such modifications and solvates and of methods for their preparation are of decisive importance. A range of active substances can exist in different crystalline but also in amorphous modifications. Polymorphism is the term used in these cases. A polymorph is a solid, crystalline phase of a compound which is characterized by a specific, uniform packing and arrangement of the molecules in the solid.

Different modifications of one and the same active substance can sometimes have different properties, for example differences in the following properties: solubility, vapor pressure, dissolution rate, stability against a phase change into a different modification, stability during grinding, suspension stability, optical and mechanical properties, hygroscopicity, crystal form and size, filterability, density, melting point, stability to decomposition, color and sometimes even chemical reactivity or biological activity.

The applicant's own attempts to convert benzoxazinone I into a crystalline solid by crystallization at first resulted in amorphous products or in complex mixtures of different crystal modifications, which could only be handled with difficulty and whose stability against uncontrolled phase change was unsatisfactory.

It has now surprisingly been found that by applying suitable crystallization conditions crystalline, stable modification of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione can be prepared, which does not display the disadvantages of the amorphous benzoxazinone I. This crystalline form is hereinafter described and termed form A.

In addition, the crystalline form A according to the invention is easier to handle than the previously known amorphous benzoxazinone I, since during production they are obtained in the form of discrete crystals. Compared to mixtures of different crystal modifications of benzoxazinone I, the pure form A displays increased stability with regard to conversion into another modification. The term "pure form A" should be understood to mean that the proportion of the form A, based on the total quantity of benzoxazinone I, is at least 90 wt. % and in particular at least 95 wt. %.

Accordingly, a first object of the present invention relates to the crystalline form A of benzoxazinone I. Also an object is a benzoxazinone I, which at least 90 wt. % in particular at least 95% consists of the crystalline form A.

The form A according to the invention can be identified by X-ray powder diffractometry on the basis of its diffraction diagram. Thus an X-ray powder diffraction diagram of form A recorded using Cu—Kα radiation (1.54178 Å) at 25° C. shows at least 3, often at least 5, in particular at least 7, and especially all of the reflections quoted in the following table as 2θ values or as interplanar spacings d:

| 2θ values | d [Å] |
|---|---|
| 8.6 ± 0.2° | 10.28 |
| 10.9 ± 0.2° | 8.16 |
| 12.9 ± 0.2° | 6.86 |
| 13.4 ± 0.2° | 6.63 |
| 14.0 ± 0.2° | 6.33 |
| 14.4 ± 0.2° | 6.14 |
| 15.5 ± 0.2° | 5.72 |
| 16.9 ± 0.2° | 5.25 |
| 18.2 ± 0.2° | 4.88 |
| 20.5 ± 0.2° | 4.33 |

Studies on single crystals of form A demonstrate that the underlying crystal structure is orthorhombic. The unit cell has the space group Pna2(1). The characteristic data of the crystal structure of form A (determined at −173° C.) are compiled in the following table.

Crystallographic Characteristics of Form A

| Parameter | Form A |
|---|---|
| Crystal system | Orthorhombic |
| Space group | P n a $2_1$ |
| a | 16.0815(4) Å |
| b | 13.1360(3) Å |
| c | 7.9675(2) Å |
| α | 90° |

-continued

| Parameter | Form A |
|---|---|
| β | 90° |
| γ | 90° |
| Volume | 1683.11(7) Å³ |
| Z | 4 |
| Density (calculated) | 1.63 g/cm³ |
| R-Factor (%) | 2.97 | a, b, c = Length of the edges of the unit cell
α, β, γ = Angles of the unit cell
Z = Number of molecules, in the unit cell Form A displays a thermogram with a characteristic melting peak in the range from 150 to 185° C. The melting point, determined as the onset of the melting peak, typically lies in the range from about 170° C. to 180° C., in particular in the range from 174 to 179° C.

The melting enthalpy is preferably in the range from 70 to 80 J/g. The values quoted here relate to values determined by differential calorimetry (differential scanning calorimetry: DSC, aluminum closed and vented cup, nitrogen flow 150 ml/min, heating rate 5 K/min).

The production of the form A of benzoxazinone I according to the invention may be effected by crystallization from a solution of benzoxazinone I in a suitable organic solvent. Suitable solvents for the crystallization of form A from a solution are organic solvents which are selected from $C_1$-$C_3$-alkanols, such as methanol, ethanol, n-propanol or isopropanol, $C_1$-$C_4$-dialkylketones, such as acetone, mono- or di-$C_1$-$C_4$-dialkylbenzenes such as ethylbenzene or xylenes, and mono- or dichlorobenzenes.

The production of the form A of benzoxazinone I according to the invention may be also be effected by crystallization from a slurry of benzoxazinone I in a suitable organic solvent. Suitable solvents for the crystallization of form A from a slurry are mixtures of water with water-miscible organic solvents which are selected from $C_1$-$C_3$-alkanols, in particular ethanol or isopropanol, $C_2$-$C_4$-alkandiols, such as 1,3-propanediol, $C_1$-$C_4$-dialkylketones, such as acetone and cyclic ethers having preferably 4 to 6 carbon atoms and 1 or 2 oxygen atoms, such as tetrahydrofurane and 1,4-dioxane.

In order to obtain form A of benzoxazinone I, the crystallization is effected at temperatures of below 60° C., in particular at most 50° C. and more preferably at most 40° C. Crystallization of form A is preferably effected under controlled conditions, i.e. the conditions of the crystallization are chosen to achieve a slow crystallization rate.

For this, in a first step i) a solution or slurry of benzoxazinone I in one of the aforesaid solvents or solvent mixtures is prepared, and then in a second step ii) crystallization of the benzoxazinone I is effected at temperatures of below 60° C., in particular at most 50° C. and more preferably at most 40° C., e.g. from −10 to 50° C., in particular from 0 to 40° C.

The concentration of benzoxazinone I in the solution or slurry used for the crystallization naturally depends on the nature of the solvent and the dissolution temperature and often lies in the range from 100 to 800 g/l. Suitable conditions can be determined by the person skilled in the art by routine experiments.

Preferably the solution or slurry used for the crystallization contains benzoxazinone I in a purity of at least 85%, often at least 90%, in particular at least 95%, i.e. the content of organic impurities which are not organic solvents is not more than 15 wt. %, often not more than 10 wt. %, and in particular not more than 5 wt. %, based on the benzoxazinone I present dissolved in the solvent.

The solution or slurry used for the crystallization is preferably essentially free from solvents other than those stated. In this context, "essentially free" means that the concentration of other solvents in the benzoxazinone I containing solution or slurry does not exceed 10 wt. %, often 5 wt. %, based on the total quantity of solvent.

The solution of benzoxazinone I can for example be prepared by the following methods:
(1) Dissolution of the benzoxazinone I, preferably in a form different from form A, in one of the aforesaid polar organic solvents, or
(2) Preparation of the benzoxazinone I by a chemical reaction and transfer of the reaction mixture, if necessary after removal of reagents and/or side products, into an organic solvent suitable according to the invention.

For the preparation of the solution by dissolution of the benzoxazinone I, essentially any known form of benzoxazinone I can be used. Often amorphous benzoxazinone I or a mixture of different crystalline modifications or a mixture of amorphous and crystalline benzoxazinone I will be used. Also suitable are other crystalline forms of benzoxazinone I and mixtures thereof, for example the form B described below and the form C also described below, not according to the invention, and mixtures of these forms as well as mixtures of form A with form B or form C of benzoxazinone I.

The dissolution of the benzoxazinone I is usually effected at temperatures in the range from 10 to 100° C., in particular from 20 to 60° C.

The solution of the benzoxazinone I can also be prepared by transferring a reaction mixture obtained by a chemical reaction, which contains the benzoxazinone I, if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the benzoxazinone I by chemical reaction of a suitable precursor of benzoxazinone I can be effected by analogy to the methods which are described in the state of the art cited at the beginning, to which full reference is hereby made.

For the preparation of a slurry of the benzoxazinone I, essentially any known form of benzoxazinone I can be used. Of course, in the preparation of form A usually a form of benzoxazinone I which is different from pure form A. However, benzoxazinone I may be used in a form already containing form A, thereby achieving a form A having a higher content of form A. Often amorphous benzoxazinone I or a mixture of different crystalline modifications or a mixture of amorphous and crystalline benzoxazinone I will be used. Also suitable are other crystalline forms of benzoxazinone I and mixtures thereof, for example the form B described below and the form C also described below, not according to the invention, and mixtures of these forms as well as mixtures of form A with form B and/or form C of benzoxazinone I.

The crystallization of form A of benzoxazinone I can be effected as follows, for example
  by cooling of the solution or slurry which contains the dissolved or dispersed benzoxazinone I,
  by concentration of the solution or slurry which contains the dissolved or dispersed benzoxazinone I, or
  by a combination of the aforesaid measures.

The crystallization is as a rule carried out until at least 80 wt. %, preferably at least 90 wt. %, of the benzoxazinone I used crystallizes out.

If the crystallization of form A is effected by cooling, the cooling rate is preferably less than 10 K/min.

The crystallization of form A can be promoted or accelerated by seeding with seed crystals of form A, for example by adding seed crystals of form A before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved benzoxazinone I.

If the crystallization is performed in the presence of seed crystals of form A, these are preferably only added at a temperature at which the saturation concentration of the benzoxazinone I in the solvent in question has been reached, i.e. at or below that temperature at which the dissolved quantity of benzoxazinone I forms a saturated solution in the solvent in question. The person skilled in the art can determine the temperature dependence of the saturation concentration in a solvent in routine experiments.

The isolation of the form A from the crystallization product, i.e. the separation of the form A from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, the form A obtained can be dried and then supplied for further processing. Often, however, the moist active substance obtained after washing, in particular an active substance moist with water, will be supplied directly for the further processing.

By means of the crystallization according to the invention, form A is obtained with a benzoxazinone I content of as a rule at least 90 wt. %, often 94 wt. %, in particular at least 96 wt. %. The content of form A, based on the total quantity of benzoxazinone I, is typically at least 90% and often at least 95% or at least 96%.

Therefore, a particular embodiment of the invention relates to 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, which consists of at least 90 wt. % and often at least 95% or at least 96% of the crystalline form A.

The crystalline form A may be mixed with other forms of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, e.g. form B and/or form C, without loosing the benefits achieved by form A. Therefore, the invention also relates to a mixture of the crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione as described herein and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione in a form which is different from form A, where the total amount of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione in the mixture is at least 90% by weight, preferably at least 94% by weight, based on the total weight of the mixture. The mixture can likewise be used for preparing formulations as described hereinafter and can likewise be used as form A itself. In the mixture, the amount of form A will generally be at least 50% by weight, in particular at least 60% by weight, e.g. form 50 to 95% by weight, in particular from 60 to 90% by weight, based on the total amount of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione contained in the mixture.

The preparation of benzoxazinone I used for the production of the form A can be effected by the process described in WO 2010/145992, to which full reference is hereby made.

In connection with the study on the crystallization of benzoxazinone I, two further crystalline modifications B and C were found. While modification B can be obtained in pure form, modification C was occasionally obtained as a mixture with forms A and B. Form B can be stably formulated and is part of another patent application.

The form B can be identified by X-ray powder diffractometry on the basis of its diffraction diagram. Thus an X-ray powder diffraction diagram of form B recorded using Cu—Kα radiation (1.54178 Å) at 25° C. shows at least 3, often at least 5, and especially all of the reflections quoted in the following table as 2θ values or as interplanar spacings d:

| 2θ values | d [Å] |
|---|---|
| 9.0 ± 0.2° | 9.85 |
| 10.9 ± 0.2° | 8.10 |
| 11.5 ± 0.2° | 7.69 |
| 12.9 ± 0.2° | 6.87 |
| 13.5 ± 0.2° | 6.56 |
| 14.9 ± 0.2° | 5.96 |
| 16.4 ± 0.2° | 5.42 |
| 16.5 ± 0.2° | 5.36 |
| 17.5 ± 0.2° | 5.06 |
| 20.3 ± 0.2° | 4.39 |

Form B displays a thermogram with a characteristic melting peak in the range from 190 to 220° C. The melting point, determined as the onset of the melting peak, typically lies in the range from about 200° C. to 210° C., in particular in the range from 203 to 208° C.

The melting enthalpy is preferably in the range from 30 to 40 J/g. The values quoted here relate to values determined by differential calorimetry (differential scanning calorimetry: DSC, aluminum closed and vented cup, nitrogen flow 150 ml/min, heating rate 5 K/min).

The production of the modification B can be principally effected analogously to the production of the modification A by running the crystallization at temperatures exceeding 60° C., in particular at temperatures of at least 80° C. or at least 90° C., e.g. from 80 to 130° C. or from 90 to 120° C.

Form B can bee obtained e.g. by crystallization from a solution or slurry of benzoxazinone I in toluene at temperatures of at least 80° C. or at least 90° C., e.g. from 80 to 130° C. or from 90 to 120° C. Apart from that crystallization from a solution of benzoxazinone I to obtain form B can be performed by analogy to the crystallization of form A, in particular regarding preparation of the solution, concentrations and measures of effecting crystallization, provided that crystallization is effected in the above temperature range.

Form B can bee obtained e.g. by crystallization from a slurry of benzoxazinone I in a mixture of water and a water-miscible solvent, selected from $C_1$-$C_3$-alkanols, in particular methanol or isopropanol, $C_2$-$C_4$-alkandiols, such as 1,3-propanediol, $C_1$-$C_4$-dialkylketones, such as acetone and cyclic ethers having preferably 4 to 6 carbon atoms and 1 or 2 oxygen atoms such as tetrahydrofurane and 1,4-dioxane at temperatures of at least 80° C. or at least 90° C., e.g. from 80 to 130° C. or from 90 to 120° C. Apart from that crystallization from a slurry of benzoxazinone I to obtain form B can be performed by analogy to the crystallization of form A, in particular regarding preparation of the slurry, concentrations and measures of effecting crystallization, provided that crystallization is effected in the above temperature range.

Pure form B is also obtained by heating the crystalline benzoxazinone I, e.g. form A of benzoxazinone I or mixtures of forms A+B+C to temperatures of at least 160° C., in particular at least 170° C., e.g. temperatures in the range from 160° C. to 210° C. or in the range from 170 to 200° C.

By means of the crystallization the form B can be obtained with a benzoxazinone I content of as a rule at least 90 wt. %, often 94 wt. %, in particular at least 96 wt. %. The content of form B, based on the total quantity of benzoxazinone I, is typically at least 90% and often at least 95% or at least 96%.

In the mixture of forms A, B and C, form C can be identified by X-ray powder diffractometry on the basis of its diffraction diagram. Thus an X-ray powder diffraction diagram recorded using Cu—Kα radiation (1.54178 Å) at 25° C. shows at least 3, often at least 5, and especially all of the reflections quoted in the following table as 2θ values or as interplanar spacings d:

| 2θ values | d [Å] |
|---|---|
| 7.6 ± 0.2° | 11.64 |
| 9.6 ± 0.2° | 9.17 |
| 11.8 ± 0.2° | 7.48 |
| 12.4 ± 0.2° | 7.11 |
| 15.2 ± 0.2° | 5.81 |
| 15.9 ± 0.2° | 5.57 |
| 16.1 ± 0.2° | 5.52 |
| 19.1 ± 0.2° | 4.64 |

The following illustrations and examples serve to illustrate the invention and should not be regarded as limiting.

Figure 1 shows an X-ray powder diffraction diagram of form A. The X-ray diffraction diagram of form A was recorded by using Panalytical X'Pert Pro diffractometer (manufacturer: Panalytical) in reflection geometry in the range from 2θ=3°-35° with increments of 0.0167° C. using Cu—Kα radiation (at 25° C.). The recorded 2θ values were used to calculate the stated interplanar spacings d. The intensity of the peaks (y-axis: linear intensity counts) is plotted versus the 2θ angle (x-axis in degrees 2θ).

Figure 2 shows an X-ray powder diffraction diagram of form B. The X-ray diffraction diagram was recorded under the conditions stated for Figure 1.

Figure 3 shows an X-ray powder diffraction diagram of a mixture of forms A+B+C. The X-ray diffraction diagram was recorded under the conditions stated for Figure 1.

The single crystal X-ray diffraction data of Form A was collected on a Bruker AXS CCD Detector using graphite Cu—Kα radiation (at −173° C.). The structure was solved using direct methods, refined and expanded by using Fourier techniques with SHELX software package (G. M. Sheldrick, SHELX-97, University of Göttingen, 1997). Absorption correction was performed with SADABS software.

DSC was performed on a Mettler Toledo DSC 822e module. Tha samples were placed in crimped but vented aluminium pans. The samples size in each case was 5 to 10 mg. The thermal behaviour was analized in the range 30-250° C. The heating rate was 5° C./min. The samples were purged with a stream of nitrogen flowing at 150 ml/during the experiment. Melting points values were confirmed by a Mettler Hot Stage in combination with a light microscope.

Preparation of Form A of Benzoxazinone I by Crystallization from a Solution in an Organic Solvent with Evaporation Examples 1 to 10

50 mg of benzoxazinone I were dissolved in 2-3 ml of the respective solvent in a test vessel. The test vessel was placed in a greenhouse and a nitrogen flow (5 l/min) was passed over the surface of the solvent. In this manner, benzoxazinone I was obtained in the form of small crystalline rods, which were isolated and analyzed by X-ray powder diffraction (XRPD). On the basis of the characteristic reflections, form A was identified.

TABLE 1

| Example | Solvent | Form | Crystal form |
|---|---|---|---|
| 1 | ethylbenzene | A | small rods |
| 2 | dichlorobenzene | A | small rods |
| 3 | chlorobenze | A | small rods |
| 4 | p-xylene | A | small rods |
| 5 | acetone | A | small rods |
| 6 | methylethylketone | A | small rods |
| 7 | methylbutylketone | A | small rods |
| 8 | methanol | A | small rods |
| 9 | ethanol | A | small rods |
| 10 | ispropanol | A | small rods |

Preparation of Form A of Benzoxazinone I by Crystallization from a Slurry in a Mixture of Water and Organic Solvent Example 11

A mixture of forms A and B of benzoxazinone I, obtained by comparative example 1 (500 mg) were suspended in 3 ml of a mixture of water and Ethanol (1:1 v/v) and the slurry was stirred for 48 h at 23° C. A slurry of crystalline material was obtained, which was filtered and analysed by XRPD and DSC. The obtained material was pure form A of benzoxazinone I.

Example 12

Form B of benzoxazinone I, obtained by example 16 (500 mg) were suspended in 3 ml of a mixture of water and tetrahydrofurane (1:1 v/v) and the slurry was stirred for 48 h at 23° C. A slurry of crystalline material was obtained, which was filtered and analysed by XRPD and DSC. The obtained material was pure form A of benzoxazinone I.

Example 13

A mixture forms A and B of benzoxazinone I, obtained by comparative example 1 (500 mg) were suspended in 3 ml of a mixture of toluene and the slurry was stirred for 48 h at 23° C. A slurry of crystalline material was obtained, which was filtered and analysed by XRPD and DSC. The obtained material was pure form A of benzoxazinone I.

Example 14

A mixture forms A and B of benzoxazinone I, obtained by comparative example 1 (500 mg) were suspended in 3 ml of a mixture of water and 1,3-propanediol (1:1 v/v) and the slurry was stirred for 48 h at 23° C. A slurry of crystalline material was obtained, which was filtered and analysed by XRPD and DSC. The obtained material was pure form A of benzoxazinone I.

Preparation of Form B of Benzoxazinone I by Crystallization from a Slurry in a Mixture of Water and Organic Solvent Example 15

Not According to the Invention

Form A of benzoxazinone I, obtained by example 12 (500 mg) were suspended in 3 ml of a mixture of water and ethanol (1:1 v/v) and the slurry was stirred for 48 h at 90° C. A slurry of crystalline material was obtained, which was filtered and analysed by XRPD and DSC. The obtained material was pure form B of benzoxazinone I.

Example 16

Not According to the Invention

A mixture forms A and B of benzoxazinone I, obtained by comparative example 1 (500 mg) were suspended in 3 ml of a mixture of water and 1,3-propanediol (1:1 v/v) and the slurry was stirred for 48 h at 90° C. A slurry of crystalline material was obtained, which was filtered and analysed by PXRD and DSC. The obtained material was pure form B of benzoxazinone I.

Preparation of Form B of Benzoxazinone I by Crystallization from a Solution in an Organic Solvent with Evaporation Example 17

Not According to the Invention 50 mg of benzoxazinone I were dissolved in 2-3 ml of toluene in a test vessel. The test vessel placed in a greenhouse and heated to 95° C. and a nitrogen flow (5 l/min) was passed over the surface of the solvent. In this manner, benzoxazinone I was obtained in the form of small crystalline plates, which were isolated and analyzed by X-ray powder diffraction (XRPD). On the basis of the characteristic reflections, form B was identified.

Preparation of Form B of Benzoxazinone I by Heating Form A

Example 18

Not According to the Invention 500 mg of form A of benzoxazinone I, obtained by example 12 were placed into an open vessel. The vessel was purged with nitrogen and sealed and than heated to 180° C. for 2 h. The obtained material was isolated and analyzed by X-ray powder diffraction (XRPD). On the basis of the characteristic reflections, form B was identified.

Preparation of a Mixture of Forms A and B of Benzoxazinone I

Comparative Example 1

50 mg of benzoxazinone I were dissolved in 2-3 ml of the respective solvent (e.g. 1-butanol, isobutanol) in a test vessel. The test vessel was placed in a greenhouse and heated to 90° C. A nitrogen flow (5 l/min) was passed over the surface of the solvent. In this manner, benzoxazinone I was obtained in the form of small crystalline rods, which were isolated and analyzed by X-ray powder diffraction (XRPD). On the basis of the characteristic reflections, a mixture of forms A and B was identified.

Just like the known amorphous benzoxazinone I, form A of benzoxazinone I as well as mixtures of form A with other form of benzoxazinone I are suitable as a herbicide, however it is superior to this as regards its handling and formulation properties. The invention thus also relates to plant protection agents containing the crystalline form A and additives usual for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water. The invention also relates to a process for combating undesired plant growth, which is characterized in that the form A of benzoxazinone I, preferably as a suitable active substance preparation, is used on plants, their habitat and/or on seeds. The invention also relates to plant protection agents containing a mixture of crystalline form A with at least one other form of benzoxazinone I and additives usual for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water. The invention also relates to a process for combating undesired plant growth, which is characterized in that the mixture of form A of benzoxazinone I with at least one other form of benzoxazinone I, preferably as a suitable active substance preparation, is used on plants, their habitat and/or on seeds. The statements made hereinafter with regard to form A of benzoxazinone I also apply to mixtures of form A with other forms of benzoxazinone I.

The plant protection agents which contain form A of benzoxazinone I combat plant growth, in particular monocotyledonous weed species such as *Avena, Lolium, Alopecurus, Phalaris, Echinochloa, Digitaria, Setaria, Cyperus* species, *Agropyron, Cynodon, Imparato* and *Sorghum*, and dicotyledonous weed species such as *Galium, Viola, Veronica, Lamium, Stellaria, Amaranthus, Sinapsis, Ipomoea, Matricaria, Abutilon, Sida, Convolvulus, Cirsium, Rumex* and *Artemisia* on non-cultivated areas very well, particularly at high application levels. In crops such as wheat, barley, rye, rice, maize, sugar beet, soya and cotton, they are active against weeds and noxious grasses, without harming the crop plants significantly. This effect occurs above all at low application levels.

Depending on the particular application method, form A of benzoxazinone I or the plant protection agents containing them can also be used in a further number of crop plants for the elimination of undesired plants. Possible crops for example include the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragara vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus armeniaca, Prunus avium, Prunus cerasus, Prunus dulcis, Prunus domestica, Prunus persica, Pyrus communis, Ribes sylvestre, Ricinus communis, Saccharum officinarum, Secale cereale, Sinapis alba, Solanum tuberosum, Sorghum bicolor* (*S. vulgare*), *Theobroma cacao, Trifolium pratense, Triticale, Triticum aestivum, Triticum durum, Vicia faba, Vitis vinifera* and *Zea mays*.

In addition, form A of benzoxazinone I or the plant protection agents containing form A can also be used in crops which through breeding including genetic engineering methods are tolerant towards the action of herbicides.

Further, form A of benzoxazinone I or the plant protection agents containing form A can also be used in crops which through breeding including genetic engineering methods are tolerant towards insect or fungal attack.

The form A of benzoxazinone I is also just as suitable as the known amorphous benzoxazinone for the defoliation and desiccation of plant parts, for example for crop plants such as cotton, potato, rape, sunflower, soya bean or field beans, in particular cotton. In this regard, embodiments of the invention also relate to agents for the desiccation and/or defoliation of plants, processes for the production of these agents and methods for the desiccation and/or defoliation of plants using the form A of benzoxazinone I.

The form A of benzoxazinone I is in particular suitable as desiccants for the desiccation of the aboveground parts of crop plants such as potato, rape, sunflower and soya bean, but also cereals. This enables completely mechanical harvesting of these important crop plants.

Also of scientific interest is the facilitation of harvesting which is enabled by the time-concentrated dropping or reduction of the strength of attachment to the tree with *citrus* fruits, olives or other species and varieties of pomaceous, stone and shelled fruit. The same mechanism, i.e. the promotion of the formation of separation tissue between fruit or leaf and shoot of the plants is also significant for well-controlled defoliation of useful plants, in particular cotton.

In addition, the shortening of the time interval in which the individual cotton plants become ripe leads to heightened fiber quality after the harvest.

Form A of benzoxazinone I or the plant protection agents containing them can for example be used in the form of directly sprayable aqueous solutions, powders, suspensions and also high concentration aqueous, oily or other suspensions, oil suspensions, pastes, dusting agents, scattering agents or granules by spraying, misting, dusting, scattering or pouring. The use forms are determined by the use purposes; in each case, they should ensure the finest possible distribution of the active substances according to the invention.

The plant protection agents according to the invention contain form A of benzoxazinone I in a purity, based on the modification in question, of at least 90 wt. %, and additives and/or carriers such as are usual for the formulation of plant protection agents. In such plant protection agents, the quantity of active substance, i.e. the total quantity of benzoxazinone I and of other active substances if necessary, normally lies in the range from 1 to 98 wt. %, in particular in the range from 10 to 95 wt. %, based on the total weight of the plant protection agent.

All solid and liquid substances which are normally used as carriers in plant protection agents, in particular in herbicide formulations are possible as carriers.

Solid carriers are for example mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder and other solid carriers.

Liquid carriers, as well as water, are also organic liquids, for example mineral oil fractions of medium to high boiling point such as kerosene and diesel oil, also coal tar oils and oils of plant or animal origin, aliphatic, cyclic and aromatic hydrocarbons, for example paraffins, tetrahydronaphthalene, alkylated naphthalenes and derivatives thereof, alkylated benzenes and derivatives thereof, including aromatic and non-aromatic hydrocarbon mixtures, for example the products marketed under the trade names Exxsol and Solvesso, alcohols such as propanol, butanol and cyclohexanol, ketones such as cyclohexanone, and strongly polar solvents, for example amides such as N-methyl-pyrrolidone.

Typical additives include surface-active substances, in particular those wetting agents, emulsifiers and dispersant (additives) normally used in plant protection agents, and also viscosity-modifying additives (thickeners and rheology modifiers), antifoaming agents, antifreeze agents, pH adjusting agents, stabilizers, anticaking agents and biocides (preservatives).

Possible surface-active substances are preferably anionic and nonionic surfactants. Protective colloids are also suitable surface-active substances.

The quantity of surface-active substances will as a rule be 0.1 to 50 wt. %, in particular 0.5 to 30 wt. %, based on the total weight of the plant protection agents according to the invention, or 0.5 to 100 wt. %, based on the total quantity of solid active substances in the formulation. Preferably, the surface-active substance include at least one anionic surface-active substance and at least one nonionic surface-active substance, and the proportion of anionic to nonionic surface-active substance typically lies in the range from 10:1 to 1:10.

Examples of anionic surfactants include alkyl aryl-sulfonates, aromatic sulfonates, for example ligninsulfonates (Borresperse types, Borregaard), phenylsulfonates, naphthalenesulfonates (Morwet types, Akzo Nobel), dibutylnaphthalenesulfonates (Nekal types, BASF), alkyl sulfates, in particular fatty alcohol sulfates, lauryl sulfates, and sulfated hexadeca-, heptadeca- and octadecanols, alkylsulfonates, alkyl ether sulfates, in particular fatty alcohol (poly)glycol ether sulfates, alkyl aryl ether sulfates, alkyl polyglycol ether phosphates, polyarylphenyl ether phosphates, alkyl-sulfosuccinates, olefin sulfonates, paraffin sulfon-ates, petroleum sulfonates, taurides, sarcosides, fatty acids, alkylnaphthalenesulfonic acids, naphthalene-sulfonic acids, ligninsulfonic acids, condensation products of sulfonated naphthalenes with formaldehyde, condensation products of sulfonated naphthalenes with formaldehyde and phenol and optionally urea and condensation products of phenolsulfonic acid with formaldehyde and urea, lignin sulfite waste liquor, alkyl phosphates, alkyl aryl phosphates, for example tristyryl phosphates, and polycarboxylates such as for example polyacrylates, maleic anhydride/olefin copolymers (for example Sokalan® CP9, BASF), including the alkali metal, alkaline earth, ammonium and amine salts of the aforesaid substances. Preferred anionic surface-active substances are those which bear at least one sulfonate group and in particular the alkali metal and ammonium salts thereof.

Examples of non-ionic surface-active substances are alkylphenol alkoxylates, in particular ethoxylates and ethoxylate-copropoxylates of octylphenol, isooctylphenol, nonylphenol and tributylphenol, di- and tristyrylphenol alkoxylates, alcohol alkoxylates, in particular fatty alcohol ethoxylates and fatty alcohol ethoxylate-copropoxylates, for example alkoxylated isotridecanol, fatty amine alkoxylates, polyoxyethylene glycerol fatty acid esters, castor oil alkoxylates, fatty acid alkoxylates, fatty acid amide alkoxylates, fatty acid polydiethanolamides, lanolin ethoxylates, fatty acid polyglycol esters, isotridecyl alcohol, ethoxylated fatty acid amides, ethoxylated fatty acid esters, alkyl polyglycosides, ethoxylated alkyl polyglycosides, sorbitan fatty acid esters, ethoxylated sorbitan fatty acid esters, glycerol fatty acid esters, lower molecular weight polyalkylene oxides such as polyethylene glycol, polypropylene oxide, polyethylene oxide co-propylene oxide di- and tri-block copolymers, and mixtures thereof. Preferred nonionic surface-active substances are fatty alcohol ethoxylates, alkyl polyglycosides, glycerol fatty acid esters, castor oil ethoxylates, fatty acid ethoxylates, fatty acid amide ethoxylates, lanolin ethoxylates, fatty acid polyglycol esters, ethylene oxide propylene oxide block copolymers and mixtures thereof.

Protective colloids are typically water-soluble, amphiphilic polymers which unlike the aforesaid surfactants typically have molecular weights over 2,000 daltons (number average). Examples thereof are proteins and denatured proteins such as casein, polysaccharides such as water-soluble starch derivatives and cellulose derivatives, hydrophobically modified starches and celluloses, for example methylcellulose, and also polycarboxylates such as polyacrylic acid, acrylic acid copolymers and maleic acid copolymers (BASF Sokalan types), polyvinyl alcohol (Mowiol types from Clariant), polyalkoxylates, polyvinylpyrrolidone, vinylpyrrolidone copolymers, polyvinyl amines, polyethyleneimines (Lupasol types from BASF) and higher molecular weight polyalkylene oxides such as polyethylene glycol, polypropylene oxides, and polyethylene oxide co-polypropylene oxide di- and tri-block copolymers.

The plant protection agents according to the invention can also contain one or more additives modifying the viscosity (rheology modifiers). These are understood in particular to mean substances and substance mixtures which impart modified flow behavior to the formulation, for example a high viscosity in the resting state and low viscosity in the moving state. The nature of the rheology modifier is determined by the nature of the formulation. As examples of rheology modifiers, inorganic substances, for example layer silicates and organically modified layer silicates such as bentonites or attapulgites (for example Attaclay®, Engelhardt Co.), and organic substances such as polysaccharides and heteropolysaccharides such as Xanthan Gum® (Kelzan® from Kelco Co.), Rhodopol® 23 (Rhone Poulenc) or Veegum® (R.T. Vanderbilt Co.) should be mentioned. The quantity of the viscosity-modifying additives is often 0.1 to 5 wt. %, based on the total weight of the plant protection agent.

Examples of antifoaming agents are the silicone emulsions known for this purpose (Silikon® SRE, Wacker Co. or Rhodorsil® from Rhodia Co.), long-chain alcohols, fatty acids and salts thereof, foam suppressants of the aqueous wax dispersion type, solid foam suppressants (so-called Compounds) and organofluorine compounds and mixtures thereof. The quantity of antifoaming agent is typically 0.1 to 1 wt. %, based on the total weight of the plant protection agent.

The plant protection agents according to the invention can also contain preservatives for stabilization. Suitable preservatives are those based on isothiazol-ones, for example Proxel® from ICI Co., or Acticide® from Thor Chemie Co. or Kathon® MK from Rohm & Hass Co. The quantity of preservative is typically 0.05 to 0.5 wt. %, based on the total weight of the SC.

Aqueous plant protection agents, i.e. those with an a aqueous carrier, often contain antifreeze agents. Suitable antifreeze agents are liquid polyols, for example ethylene glycol, propylene glycol or glycerine, and urea. The quantity of antifreeze agent is as a rule 1 to 20 wt. %, in particular 5 to 10 wt. %, based on the total weight of the aqueous plant protection agent.

If the plant protection agents containing the crystalline modification A of benzoxazinone I are used for seed treatment, they can also contain normal components such as are used for seed treatment, for example in dressing or coating. In addition to the aforesaid components, these include in particular colorants, adhesives, fillers and plasticizers.

All the dyes and pigments usual for such purposes are possible as colorants. Both pigments of low solubility in water and also dyes soluble in water are usable here. As examples, the dyes and pigments known under the names Rhodamin B, C.I. Pigment Red 112 and C.I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 10 and Basic Red 108 may be mentioned. The quantity of colorant will normally not constitute more than 20 wt. % of the formulation and preferably lies in the range from 0.1 to 15 wt. %, based on the total weight of the formulation.

All binders normally usable in dressings come under consideration as adhesives. Examples of suitable binders include thermoplastic polymers such as poly-vinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropyl cellulose and starch derivatives and modified starches, dextrins, maltodextrins, alginates and chitosans, and also fats, oils, proteins, including casein, gelatin and zein, gum Arabic and shellac. The adhesives are preferably plant-compatible, i.e. they exhibit no, or no significant, phytotoxic effects. The adhesives are preferably biodegradable. The adhesive is preferably selected such that it acts as a matrix for the active components of the formulation. The quantity of adhesive will normally not constitute more than 40 wt. % of the formulation and preferably lies in the range from 1 to 40 wt. % and in particular in the range from 5 to 30 wt. %, based on the total weight of the formulation.

In addition to the adhesive, the formulation for seed treatment can also contain inert fillers. Examples of these are the aforesaid solid carriers, in particular finely divided inorganic materials such as clays, chalk, bentonite, kaolin, talc, perlite, mica, silica gel, diatomaceous earth, quartz powder and montmorillonite but also fine-particle organic materials such as wood flour, cereal flour, active charcoal and the like. The quantity of filler is preferably selected such that the total quantity of filler does not exceed 70 wt. %, based on the total weight of all non-volatile components of the formulation. Often, the quantity of filler lies in the range from 1 to 50 wt. %, based on the total weight of all non-volatile components of the formulation.

In addition, the formulation for seed treatment can also contain a plasticizer which increases the flexibility of the coating. Examples of plasticizers are oligomeric polyalkylene glycols, glycerine, dialkyl phthalates, alkylbenzyl phthalates, glycol benzoates and comparable compounds. The quantity of plasticizer in the coating often lies in the range from 0.1 to 20 wt. %, based on the total weight of all non-volatile components of the formulation.

A preferred embodiment of the invention relates to liquid formulations of the form A of benzoxazinone I. In addition to the solid active substance phase, these have at least one liquid phase, in which benzoxazinone I is present in form A in the form of dispersed fine particles. Possible liquid phases are essentially water and those organic solvents in which the form A is only slightly soluble, or insoluble, for example those wherein the solubility of the form A or form C at 25° C. and 1013 mbar is not more than 1 wt. %, in particular not more than 0.1 wt. %, and especially not more than 0.01 wt. %.

According to a first preferred embodiment, the liquid phase is selected from water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydrofuran, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain benzoxazinone I in the form of modification A in a finely divided particulate form, wherein the particles of the form A are present suspended in an aqueous phase. The size of the active substance particles, i.e. the size which 90 wt. % of the active substance particles do not exceed, here typically lies below 30 μm, in particular below 20 μm. Advantageously, in the SCs according to the invention, at least 40 wt. % and in particular at least 60 wt. % of the particles have diameters below 2 μm.

In such SCs the quantity of active substance, i.e. the total quantity of benzoxazinone I and of other active substances if necessary, usually lies in the range from 10 to 70 wt. %, in particular in the range from 20 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a second preferred embodiment, the liquid phase consists of non-aqueous organic solvents in which the solubility of the form A of benzoxazinone I at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like. Accordingly, the present invention relates also to agents for plant protection in the form of a non-aqueous suspension concentrate, which will also be referred to below as OD (oil-dispersion). Such ODs contain the form A of benzoxazinone I in a finely divided particulate form, wherein the particles of the form A are present suspended in a non-aqueous phase. The size of the active substance particles, i.e. the size which 90 wt. % of the active substance particles do not exceed, here typically lies below 30 μm, in particular below 20 μm. Advantageously, in the non-aqueous suspension concentrates, at least 40 wt. % and in particular at least 60 wt. % of the particles have diameters below 2 μm.

In such ODs, the quantity of active substance, i.e. the total quantity of benzoxazinone I and of other active substances if necessary, usually lies in the range from 10 to 70 wt. %, in particular in the range from 20 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

The form A of benzoxazinone I according to the invention can also be formulated as solid plant protection agents. These include powder, scattering and dusting agents but also water-dispersible powders and granules, for example coated, impregnated and homogenous granules. Such formulations can be produced by mixing or simultaneous grinding of the form A of benzoxazinone I with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers. For the production of solid formulations of benzoxazinone I of form A, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of benzoxazinone and of other active substances if necessary, usually lies in the range from 10 to 70 wt. %, in particular in the range from 20 to 50 wt. %, based on the total weight of the solid formulation.

The application of the form A of benzoxazinone I or the herbicidal agents containing them is effected, if the formulation is not already ready for use, in the form of aqueous spray fluids. These are prepared by dilution of the aforesaid formulations containing the form A of benzoxazinone I with water. The spray fluids can also contain other components in dissolved, emulsified or suspended form, for example fertilizers, active substances of other herbicidal or growth-regulating active substance groups, other active substances, for example active substances for combating animal pests or phyto-pathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention.

The application of the form A of benzoxazinone I or of the plant protection agents containing them can be effected in a pre-emergence or in a post-emergence method. If benzoxazinone I is less tolerable for certain crop plants, application techniques can be used wherein the herbicidal agents are sprayed using the spraying equipment in such a manner that the leaves of the sensitive crop plants are as far as possible not hit, while the active substances reach the leaves of undesired plants growing under them or the uncovered soil surface (post-directed, lay-by).

The quantities of benzoxazinone I applied are 0.001 to 3.0 kg active substance per hectare, preferably 0.01 to 1.0 kg active substance (a·S)/ha, depending on the treatment aim, season, target plants and growth stage.

In a further embodiment, the application of the form A of benzoxazinone I or the plant protection agent containing them can be effected by treatment of seed.

Treatment of seed essentially includes all techniques with which the person skilled in the art is familiar (seed dressing, seed coating, seed dusting, seed soaking, seed film coating, seed multilayer coating, seed encrusting, seed dripping and seed pelleting) on the basis of form A of benzoxazinone I, or agents prepared therefrom. Here the plant protection agents can be applied diluted or undiluted.

The term seed includes seed of all types, for example grains, seeds, fruits, tubers, cuttings and similar forms. Preferably, the term seed here describes grains and seeds.

As seed, seed of the crop plants mentioned above but also the seeds of transgenic plants or those obtained by conventional breeding methods can be used.

For the seed treatment, benzoxazinone I is normally used in quantities of 0.001 to 10 kg per 100 kg of seed.

To broaden the spectrum of action and to achieve synergistic effects, the form A of benzoxazinone I can be mixed and applied together with many members of other herbicidal or growth regulating active substance groups. In addition, it can be advantageous to formulate or apply benzoxazinone together with safeners. With regard to such combinations, full reference is made to WO 2010/145992.

In addition, it can be of value to apply the form A alone or in combination with other herbicides also mixed with still further plant protection agents, together for example with agents for combating pests or phytopathogenic fungi or bacteria. Also of interest is the miscibility with mineral salt solutions which are used for the elimination of nutritional and trace element deficiencies. Additives such as non-phytotoxic oils and oil concentrates can also be added.

The invention claimed is:

1. A crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, which in an X-ray powder diffraction diagram at 25° C. and Cu—Kα radiation displays at least 3 of the following reflections, quoted as 2θ values: 8.6±0.2°, 10.9±0.2°, 12.9±0.2°, 13.4±0.2°, 14.0±0.2°, 14.4±0.2°, 15.5±0.2°, 16.9±0.2°, 18.2±0.2° and 20.5±0.2°.

2. The crystalline form A as claimed in claim 1 with a content of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-diose of at least 94 wt. %.

3. 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione consisting of at least 90 wt. % of the crystalline form A.

4. A process for the production of the crystalline form A as claimed in claim 1, comprising:
  i) preparation of a slurry of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione in a mixture of water with at least one water miscible organic solvent selected from cycloaliphatic ethers, $C_1$-$C_3$-alkanols and $C_2$-$C_4$-alkandiols;
  ii) effecting a crystallization of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione at a temperature below 60° C.

5. A process for the production of the crystalline form A as claimed in claim 1, comprising:
  i) preparation of a solution of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione in an organic solvent selected from $C_1$-$C_3$-alkanols, $C_1$-$C_4$-dialkylketones, mono- or di-$C_1$-$C_4$-dialkylbenzenes and mono- or dichlorobenzenes;
  ii) effecting a crystallization of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione at a temperature below 60° C.

6. A mixture of the crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione as claimed in claim 1 and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-diene in a form which is different from form A, where the total amount of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-diene in the mixture is at least 90% by weight based on the total weight of the mixture.

7. A plant protection agent containing the crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione as claimed in claim 1, and one or more additives customary for the formulation of plant protection agents.

8. A plant protection agent containing 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione in its crystalline form A as claimed in claim 1 and one or more additives customary for the formulation of plant protection agents.

9. The plant protection agent as claimed in claim 7 in the form of an aqueous suspension concentrate.

10. The plant protection agent as claimed in claim 7 in the form of a non-aqueous suspension concentrate.

11. The plant protection agent as claimed in claim 7 in the form of a powder or granules dispersible in water.

12. A method for combating undesired plant growth, wherein the crystalline form A of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione as claimed in claim 1 is applied to plants to be controlled or to their habitat.

13. The method of claim 12, wherein the crystalline form A has a content of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione of at least 94 wt. %.

14. The method of claim 13, wherein the crystalline form A has a content of 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione consisting of at least 90 wt. % of the crystalline form A.

\* \* \* \* \*